US008080217B2

(12) United States Patent
Morrison

(10) Patent No.: US 8,080,217 B2
(45) Date of Patent: Dec. 20, 2011

(54) STORAGE CONTAINER FOR BIOLOGICAL SAMPLE AND METHOD FOR ANALYSING THE SAMPLE

(75) Inventor: Allan D. Morrison, Coopers Plains (AU)

(73) Assignee: Bizpac (Australia) Pty Ltd, Coopers Plain (AU)

( * ) Notice: Subject to any disclaimer, the term of this patent is extended or adjusted under 35 U.S.C. 154(b) by 1145 days.

(21) Appl. No.: 10/648,088

(22) Filed: Aug. 26, 2003

(65) Prior Publication Data
US 2004/0126281 A1  Jul. 1, 2004

(30) Foreign Application Priority Data
Aug. 26, 2002  (AU) ................................ 2002951034

(51) Int. Cl.
*G01N 33/00* (2006.01)
(52) U.S. Cl. ......... 422/400; 422/500; 422/501; 422/502
(58) Field of Classification Search .................. 422/100, 422/101, 102, 99, 400, 500, 501, 502
See application file for complete search history.

(56) References Cited

U.S. PATENT DOCUMENTS

| 4,817,800 | A | * | 4/1989 | Williams et al. .............. 206/484 |
| 5,460,057 | A |   | 10/1995 | Ostrup |
| 5,624,554 | A | * | 4/1997 | Faulkner et al. .............. 210/232 |
| 5,872,713 | A | * | 2/1999 | Douglas et al. ................. 702/85 |
| 6,416,715 | B1 | * | 7/2002 | Gambert et al. .............. 422/100 |
| 6,750,039 | B1 | * | 6/2004 | Bargoot et al. ................. 435/34 |
| 6,818,180 | B2 | * | 11/2004 | Douglas et al. ................. 422/58 |
| 6,884,397 | B2 | * | 4/2005 | Day .............................. 422/102 |

FOREIGN PATENT DOCUMENTS
WO  WO 99/65625 A1  12/1999
* cited by examiner

*Primary Examiner* — Sam P Siefke
(74) *Attorney, Agent, or Firm* — Fulbright & Jaworski L.L.P.

(57) ABSTRACT

A storage container (10) for storage of a biological sample (20) for analysis, wherein said container comprises a body (11) defining a compartment for storage of said sample; a platform (12) for retaining the sample (20), which platform is slidably received within the compartment; a closure (13) for an opening in the body (11) through which the platform (12) may be withdrawn from the compartment; and a locking mechanism (18) for the container whereby manual access to the sample is prevented after locking. Suitably a sample identifier (15) is provided for securing in the container (10) with the sample (20), and a portion (19) of the container is transparent to permit reading the sample identifier. The storage container (10) is desirably adapted for processing, such as sampling, by an automated test apparatus (21) when said container is interlocked in a docking station of the test apparatus.

25 Claims, 2 Drawing Sheets

STORAGE CONTAINER FOR BIOLOGICAL SAMPLE AND METHOD FOR ANALYSING THE SAMPLE

CROSS-REFERENCE TO RELATED APPLICATIONS

Figure 1:
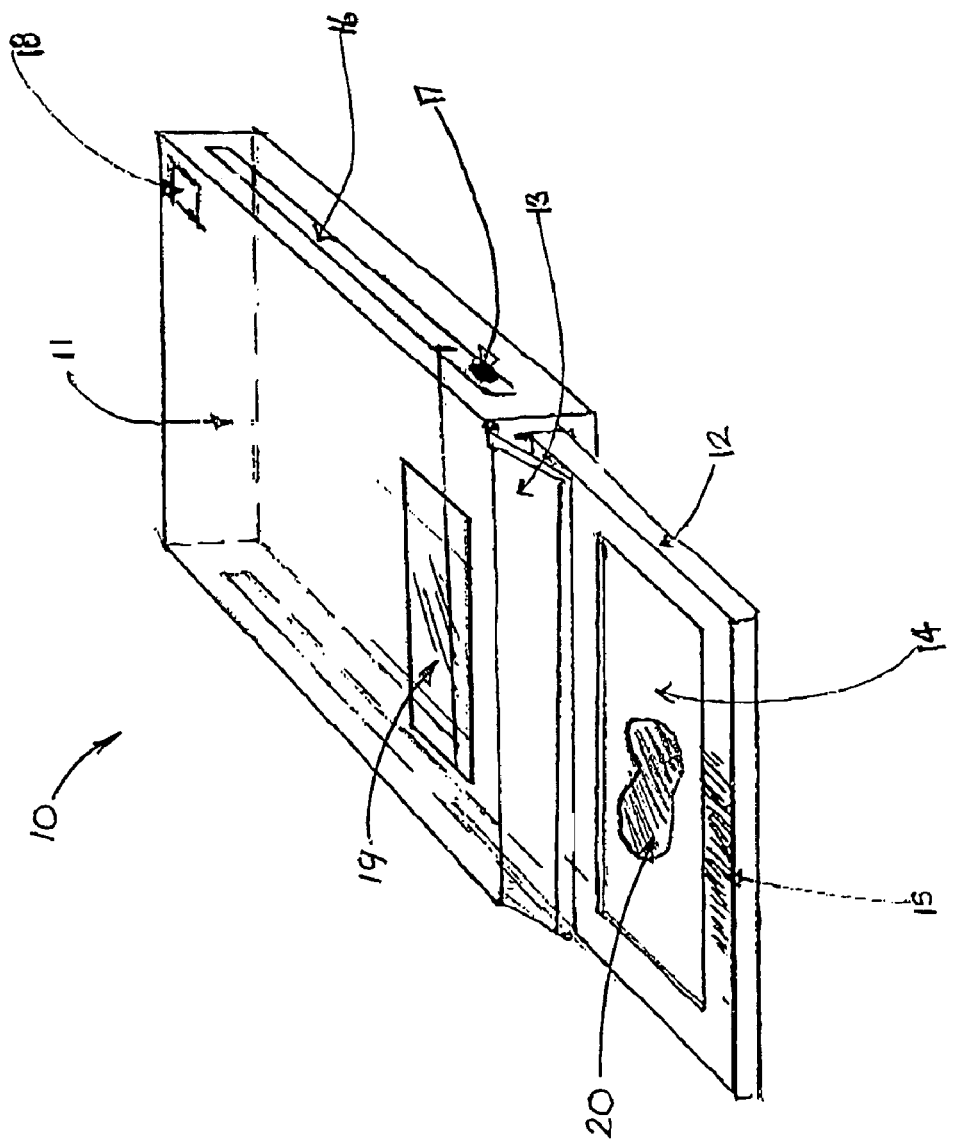

Priority is hereby claimed to co-pending Australian application serial number 2002951034, filed 26 Aug. 2002, which is incorporated herein.

See also, U.S. patent application Ser. No. 09/719,754, filed 7 Feb. 2002, which is also incorporated herein.

BACKGROUND OF THE INVENTION

1. Field of the Invention

The present invention relates to the sampling of materials for analysis. In particular, although not exclusively, the present invention relates to a method for securely holding biological samples for sampling, automated processing and storage purposes and to a storage container for same.

2. Discussion of the Background Art

Materials that have been collected in the form of samples may often need to be stored for extended periods, often to be subjected to further analysis. Currently, handling of samples such as those taken on a piece of filter paper are placed in a paper envelope, manually sealed and a barcode placed upon the envelope. Such envelopes are then typically sent to a central processing point for storage and/or analysis as required.

There is a risk that the storage of such samples for extended periods may result in contamination, either inadvertent or deliberate. There is also a risk that the samples may be misidentified after manual handling or an extended period of storage, caused either by tampering or merely aging.

Accordingly, it is desirable that samples may be stored for an extended period in a secure container and can be identified and analysed intermittently over a period of time, without compromising the integrity of the stored sample.

Furthermore, removal of samples from the paper envelopes of the prior art for processing is a manual and time consuming task, and one which is a significant hindrance to automation of sample processing.

SUMMARY OF THE INVENTION

Object of the Invention

It is an object of the invention to provide an improved method of analysing a biological sample and an improved container for securely holding said sample, which addresses the drawbacks of prior art methods and storage apparatus.

Disclosure of the Invention

According to one broad form of the present invention, there is provided a method of analysing a sample comprising the steps of: placing a sample into a container, said container having a compartment for receiving the sample, and closing said container; docking said container with a testing apparatus, said testing apparatus having and an interlock means selected to prevent tampering with said sample during the sampling thereof; accessing the compartment and analysing the sample; closing access to the compartment prior to removing the container from the interlock means and returning the container to storage.

In another broad form, the present invention provides a storage container for storage of samples for analysis, wherein said container comprises: a compartment for storage of said sample; a closure for sealing said compartment; wherein the closure may be sealed for securing the sample within the container. Suitably said sealed closure incorporates a locking mechanism whereby the sealed closure is manually inoperable after locking.

The present invention also includes a testing apparatus having a docking station including an interlock means selected to prevent tampering with a sample contained in a compartment of a container during access to the sample for processing by said testing apparatus. Suitably, the interlock means is electronic in form.

This invention has particular but not exclusive application to biological samples that may be used in medical diagnostic tests. For example, medical tests may be conducted using samples of blood, saliva or urine. The samples may comprise dried blood, saliva or urine retained by a piece of paper card or a swab.

The processing of the samples may be conducted by punching a selected portion of the sample from the piece of card or swab which punched section is then removed for analysis. The remaining sample may be returned to the storage space in the container for later analysis. In our earlier filed International Patent Application No. PCT/AU99/00485 (WO 99/65625), now proceeding as U.S. patent application Ser. No. 09/719,754, a punching apparatus is described for this purpose.

In a preferred embodiment of the present invention a sample filter paper card may be securely locked into a container immediately after it has been collected.

In a preferred embodiment at least a portion of the container may be transparent and an identifier may be placed inside the container whereby, the sample identifier is inaccessible and resistant to external tampering. For example, an identification label carrying a barcode may be affixed to the inside of the container. In another example, the identification means may be electronic such as a radio frequency identification (RFID) tag.

The sample, retained on a filter paper card, may be fixed to a small sliding platform inside the container whereby when the sample is processed, the sliding platform may be withdrawn from the container whilst the container is docked with the testing apparatus. Suitably the platform is only able to be partially withdrawn from the container in order to access to the sample, such as by a sampling device which removes a portion of the sample.

In a preferred configuration of the present invention the container may be unlocked with a key that is integral with the testing apparatus. On docking with the testing apparatus and interlocking therewith, the key may be positioned or operated to allow a sampling device access to the sample.

The container may include a memory to record the number of times the sample has been accessed, suitably including the time and date of each accession. This record may be achieved by using a physical tab that is broken or by using a form of electronic memory.

BRIEF DETAILS OF THE DRAWINGS

Figure 2:
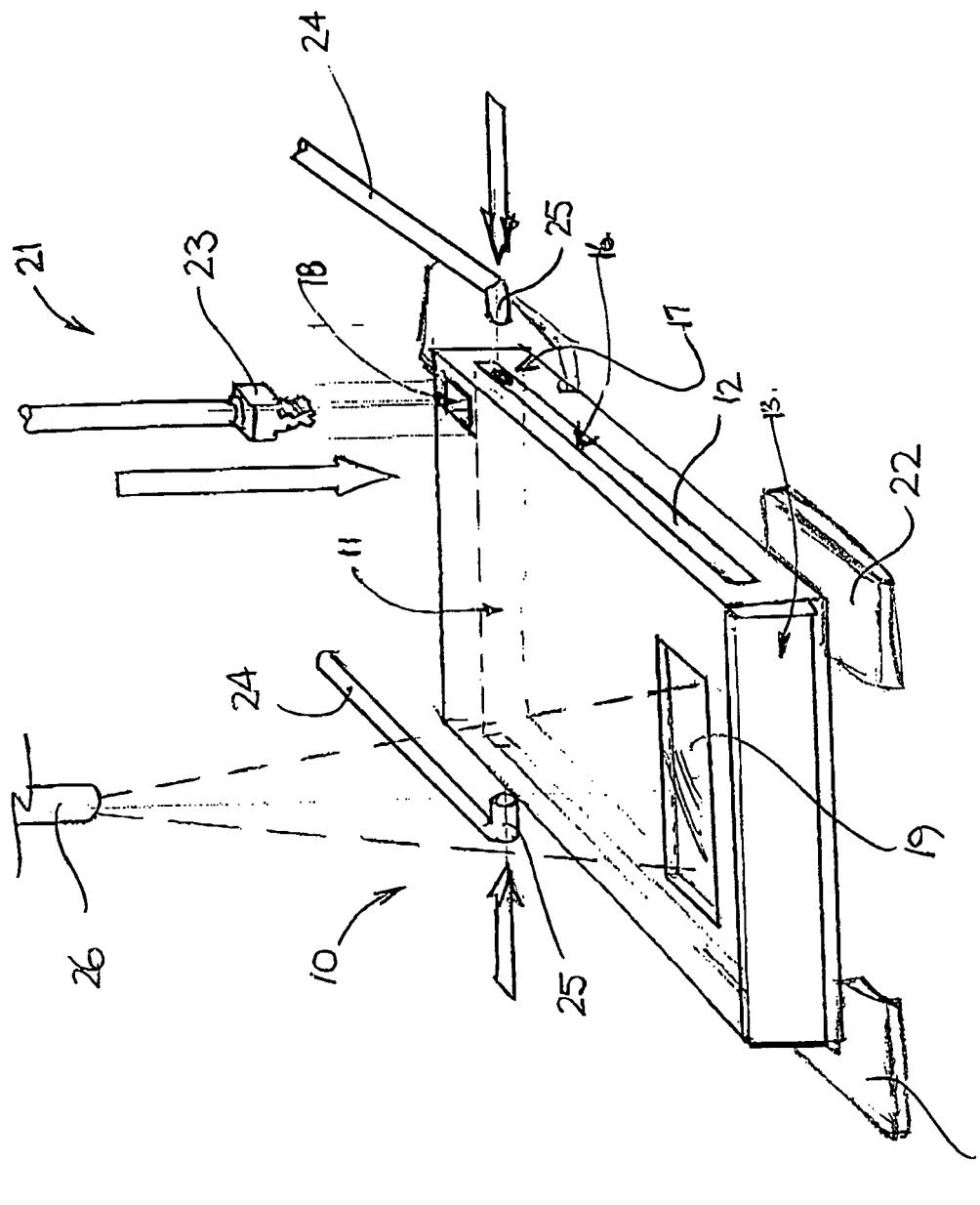

In order that the invention may be more readily understood and put into practical effect, reference will now be made to the accompanying drawings which illustrate a preferred embodiment of the invention and wherein:

FIG. 1 is a pictorial view of a container of a first embodiment of the invention; and FIG. 2 is a pictorial view of the container of a first embodiment positioned in the docking station of a testing apparatus.

DESCRIPTION OF EMBODIMENTS OF THE INVENTION

The container 10 of the embodiment depicted in FIG. 1 includes a body 11 which defines a compartment for housing a platform 12, which platform is able to be withdrawn into the compartment by sliding engagement with the body 11. The container of the embodiment has two relatively large dimensions (for example 54 mm wide×65 mm deep) and one small dimension (for example 6 mm high), and is generally in the form of a cassette. A container having these approximate dimensions is suited to automated handling and storage of biological samples.

The container 10 further includes a closure, here in the form of a door member 13 having a long edge pivotally coupled to the body 11, over the access opening for the platform. The closure is provided for sealing the compartment against the entry of dust, moisture and other contaminants. It will be appreciated that, in alternative embodiments, the door member may extend over an upper surface of the container body in the form of a lid.

The sliding platform 12 of the embodiment includes a central recess or aperture for receiving a medium, such as filter paper card 14, for retaining a dried sample 20 of blood, saliva or urine. The platform 12 may be in the form of a frame allowing access to both faces of the medium, such as for punching a portion of the sample. In other forms of the invention, the samples may comprise keratinous matter or flesh, such as may be required for forensic purposes.

In order to identify the source of the sample 20 an identifier, such as a barcode 15, is provided on the platform 12. To allow identification when the sample on the platform 12 is stored in the compartment, the body 11 includes a transparent portion 19 for reading the barcode 15 or other identifier. It is desirable for both the identifier and the medium retaining the sample 20 to be fixed to the platform 12.

The body 11 of the container 10 further includes slots 16 in side walls thereof allowing mechanical access to engagement means, such as a hole or socket 17, provided in each side of the platform 12. The hole or socket 17 is adapted for engagement by a mechanical device in order to withdraw the platform 12 from the container 10. Suitably the mechanical withdrawal device will be part of an automated test apparatus 21 (portions of which are depicted in FIG. 2) for analysing a portion of the sample 20 retained on the filter paper 14 or other medium.

Turning to FIG. 2, the test apparatus 21 will desirably include one or more docking stations, including positioning means 22, for containers 10 of the invention. The docking station will also include an interlock means which cooperates with a locking device 18 provided on the container 10. In one form the interlocking means will include a key 23 to release the locking device 18 and allow the platform 12 to be withdrawn from the container 10 for access to the sample 20 stored in the compartment of the container.

The testing apparatus of the embodiment includes a pair of mechanically actuated fingers 24 having spigot portions 25, which protrude through the slots 16 in the container 10, for engagement with sockets 17 provided in each side of the platform 12 when positioned in a docking station. Upon release of the locking device 18, the mechanical fingers 24 are able to withdraw the platform 12 from the container 10 to enable sample processing. It will be appreciated that the testing device may further include transport means for rapidly transferring containers to and from the docking station(s).

If required, the locking device 18 will also secure the closure door 13 to the compartment. However, in an alternative form the closure may be formed by a resilient cover, formed of rubber and having a central longitudinal slit, permitting mechanical withdrawal of the sliding platform 12 when released by the interlock.

The testing apparatus of the embodiment further includes a bar code reader, the scanning head 26 of which reader is depicted in FIG. 2. The bar code reader is arranged for reading a sample identification bar code 15 through the transparent window 19 provided in the body 11 of the storage container 10, when delivered to the docking station.

The container 10 may include a memory (not shown) to record the number of times the sample has been accessed, suitably including the time and date of each accession. This record can be achieved by using a form of electronic memory, such as non-volatile RAM, which is updated upon docking with the testing apparatus. If required, the identity or location of the particular testing apparatus may also be recorded. The electronic memory may also include sample identification data in some embodiments or be associated with an RFID tag. A more simplified record may merely entail using a physical tab that is broken or a mechanical counter which is incremented upon accessing the compartment.

Advantageously the present invention will permit the rapid processing of a large number of samples in comparison to the current practice. Current practice generally requires a sample to be taken on a piece of filter paper which has a wrapper that folds around the sample part of the card. This is then placed in a paper envelope and sealed with sticking tape and a barcode placed upon the envelope.

The envelope is then sent to a central processing point where, at an appropriate time, the envelope is opened, the sample card is unwrapped and a small part of the sample is then punched out into a micro titre plate. This process, including the punching may take up to half a minute. The present invention has the potential to significantly reduce the elapsed time of the sampling process, possibly down to less than ten seconds, in particular by automating handling of the sample. The automated handling can include identifying the sample, and moving the sample in and out of a protective container ready for immediate punching of a portion of the sample in situ.

Whilst the present application has been described in relation to the analysis of biological samples persons skilled in the art will readily understand that it will have applications in other fields, such as environmental monitoring.

It will of course be understood that the above has been given by way of illustration and that all modifications and variations thereto as would be apparent to persons skilled in the art are deemed to fall within the broad scope and ambit of this invention, as defined in the following claims.

The invention claimed is:

1. A storage system for storage of a biological sample for analysis, said system comprising:
   a filter paper card for retaining the biological sample, said card having an upper face and a lower face;
   a platform having an upper surface, a lower surface and a recess through said upper and lower surfaces, said recess being configured to allow access to both faces of said card when said card is in said platform; and
   a container including a compartment comprising walls defining an opening, wherein the opening is covered by a door coupled to said container; and wherein said opening is adapted to receive said platform, said door movable between a closed position wherein said platform is sealed within the compartment from the surrounding area outside the compartment, and an open position wherein said platform is exposed, and wherein said platform is configured to be only partially withdrawn from said container.

2. The storage system of claim 1, further comprising a testing apparatus having mechanical extensions for partially withdrawing said platform from said container.

3. The storage system of claim 1, wherein said platform is adapted to be lockably secured in place within the container.

4. The storage system of claim 1, further comprising a closure for sealing said compartment and a locking mechanism whereby the closure is manually inoperable after locking.

5. The storage system of claim 1, further comprising an identifier located inside the container for identifying the sample, said identifier being visible when viewed from outside said container.

6. The storage system of claim 5, wherein the sample identifier includes a barcode.

7. The storage system of claim 1, further comprising a sampling device, wherein said sampling device includes at least one extension adapted to interdigitate with said platform to prevent said platform from being completely withdrawn from the container.

8. The storage system of claim 1, further comprising an electronic memory to record the number of times the sample has been accessed.

9. The storage system of claim 8, wherein the electronic memory is adapted to record the time and date of each accession.

10. A storage system for storage of a biological sample for analysis, wherein said system comprises:
a filter paper card; and
a container comprising: a body defining a compartment for storage of said sample,
wherein said compartment comprises walls defining an opening and the opening is covered by a door coupled to said container; and
a platform having a recess adapted to receive said filter paper card for retaining the sample, which platform is slidably received within the compartment and said door is movable between a closed position wherein said platform is sealed within the compartment from the surrounding area outside the compartment, and an open position wherein said platform is exposed, and wherein said platform is configured to be only partially withdrawn from said container.

11. The storage system of claim 10, said platform comprises at least one indentation for securing the platform within the compartment.

12. The storage system of claim 11, in combination with a testing apparatus having mechanical extensions for partially withdrawing said platform from said container, said extensions being adapted to engage said at least one indentation of said platform.

13. The storage system and testing apparatus combination of claim 12, wherein said testing apparatus includes a scanner for identifying the sample.

14. The storage system of claim 10, further comprising a sampling device, wherein said sampling device includes at least one extension adapted to interdigitate with said platform to prevent said platform from being completely withdrawn from the container.

15. The storage system of claim 10, wherein said platform may be lockably secured in place within the container.

16. The storage system of claim 10, further comprising an identifier located inside the container for identifying the sample, said identifier being visible when viewed from outside said container.

17. The storage system of claim 16, wherein the sample identifier includes a barcode.

18. The storage system of claim 10, further comprising an electronic memory to record the number of times the sample has been accessed.

19. The storage system of claim 18, wherein said electronic memory is adapted to record the time and date of each accession.

20. A storage system for storage of a biological sample for analysis, said system comprising:
a filter paper card for retaining the sample; and
a container comprising:
a frame having a recess adapted to receive the filter paper card for retaining the sample, said frame including at least one indentation; and
a body defining a compartment for storage of said frame, said body having walls defining an access opening for permitting movement of a portion of said frame into and out of said body, said access opening covered by a door coupled to said container;
said body including at least one aperture for accessing said at least one indentation of said frame to facilitate movement of said frame relative to said body, said door being movable between a closed position wherein said platform is sealed within the compartment from the surrounding area outside the compartment, and an open position wherein said platform is exposed, and wherein said frame is configured to be only partially withdrawn from said container.

21. The system of claim 20, wherein said at least one indentation is a socket configured to receive a mechanical extension from an automated testing apparatus.

22. The system of claim 20, wherein said card has an upper face and a lower face, said recess being configured to allow access to both faces of the card when the card is in said frame.

23. The storage system of claim 1 wherein said door is pivotally coupled to said container.

24. The storage system of claim 10 wherein said door is pivotally coupled to said container.

25. The storage system of claim 20 wherein said door is pivotally coupled to said container.

* * * * *